United States Patent
Baik et al.

(10) Patent No.: US 10,561,619 B2
(45) Date of Patent: Feb. 18, 2020

(54) PHARMACEUTICAL COMPOSITION COMPRISING DUTASTERIDE AND PROPYLENE GLYCOL MONOLAURATE AND PREPARATION METHOD OF THE SAME

(71) Applicant: Yuyu Pharma, Inc., Jecheon-si, Chungcheongbuk-do (KR)

(72) Inventors: Tae Gon Baik, Seoul (KR); Seyeon Kim, Suwon-si (KR); Kyeongjin Ahn, Seoul (KR); Ju-Hee Kim, Suwon-si (KR); Young-Joon Park, Gwacheon-si (KR)

(73) Assignee: Yuyu Pharma, Inc., Jecheon-si (KR)

( * ) Notice: Subject to any disclaimer, the term of this patent is extended or adjusted under 35 U.S.C. 154(b) by 0 days.

(21) Appl. No.: 16/065,830

(22) PCT Filed: Dec. 29, 2016

(86) PCT No.: PCT/KR2016/015533
§ 371 (c)(1),
(2) Date: Jun. 25, 2018

(87) PCT Pub. No.: WO2017/116190
PCT Pub. Date: Jul. 6, 2017

(65) Prior Publication Data
US 2019/0008785 A1    Jan. 10, 2019

(30) Foreign Application Priority Data

Dec. 31, 2015 (KR) .................. 10-2015-0190815

(51) Int. Cl.
*A61K 9/48* (2006.01)
*A61K 31/568* (2006.01)

(52) U.S. Cl.
CPC .......... *A61K 9/4858* (2013.01); *A61K 9/4825* (2013.01); *A61K 9/4833* (2013.01); *A61K 31/568* (2013.01)

(58) Field of Classification Search
CPC .. A61K 9/4858; A61K 9/4866; A61K 9/4833; A61K 9/4825; A61K 31/568
See application file for complete search history.

(56) References Cited

U.S. PATENT DOCUMENTS

| | | |
|---|---|---|
| 2005/0181041 A1 | 8/2005 | Goldman |
| 2008/0317844 A1 | 12/2008 | Dudley et al. |
| 2012/0328702 A1 | 12/2012 | Edelson et al. |
| 2013/0210869 A1* | 8/2013 | Pellegrini ............ A61K 9/1676 514/362 |

FOREIGN PATENT DOCUMENTS

| | | |
|---|---|---|
| JP | 2007516259 A | 6/2007 |
| JP | 2014528900 A | 10/2014 |
| KR | 20130124414 A | 11/2013 |
| KR | 101679992 B1 | 11/2016 |
| WO | 9908666 A2 | 2/1999 |
| WO | 2010092596 A1 | 8/2010 |
| WO | WO 2010092596 A1 * | 8/2010 |
| WO | 2012076516 A1 | 6/2012 |
| WO | 2017043913 A1 | 3/2017 |
| WO | 2017116190 A1 | 7/2017 |
| WO | 2017196148 A1 | 11/2017 |

OTHER PUBLICATIONS

International Search Report received in PCT/KR2016/015533 dated Apr. 7, 2017.
Written Opinion received in PCT/KR2016/015533 dated Apr. 7, 2017.
Office Action received in JP2018547245 dated Apr. 13, 2019.
Written Opinion received in JP2018547245 dated Jul. 12, 2019.
Choo, et al., "Formulation and in vivo evaluation of a self-microemulsifying drug delivery system of dutasteride", Mar. 13, 2013, pp. 203-209, vol. 63, No. 4, Publisher: Drug Res (Stuttg).
Supplementary European Search Report and Opinion received in EP16882142 dated Jul. 1, 2019.

* cited by examiner

*Primary Examiner* — Blessing M Fubara
(74) *Attorney, Agent, or Firm* — Suzannah K. Sundby, Esq.; Canady + Lortz LLP

(57) ABSTRACT

The present invention relates to a pharmaceutical composition comprising dutasteride and propylene glycol monolaurate, which improves the stability of dutasteride, which is a poorly soluble drug as a 5-alpha reductase inhibitor, and a process for its preparation. More particularly, the present invention also relates to a capsule formulation which is smaller in size than a commercial dutasteride capsule formulation (AVODART®), but has the equivalent dissolution rate by preparing a pharmaceutical composition comprising propylene glycol monolaurate and dutasteride, which can improve the stability of the dutasteride. A dutasteride formulation having enhanced patient's compliance and improved stability and a method for producing the same are provided.

7 Claims, 1 Drawing Sheet

[Fig. 1]
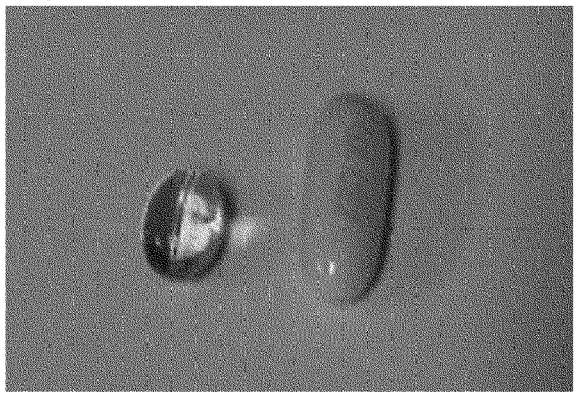
[Fig. 2]
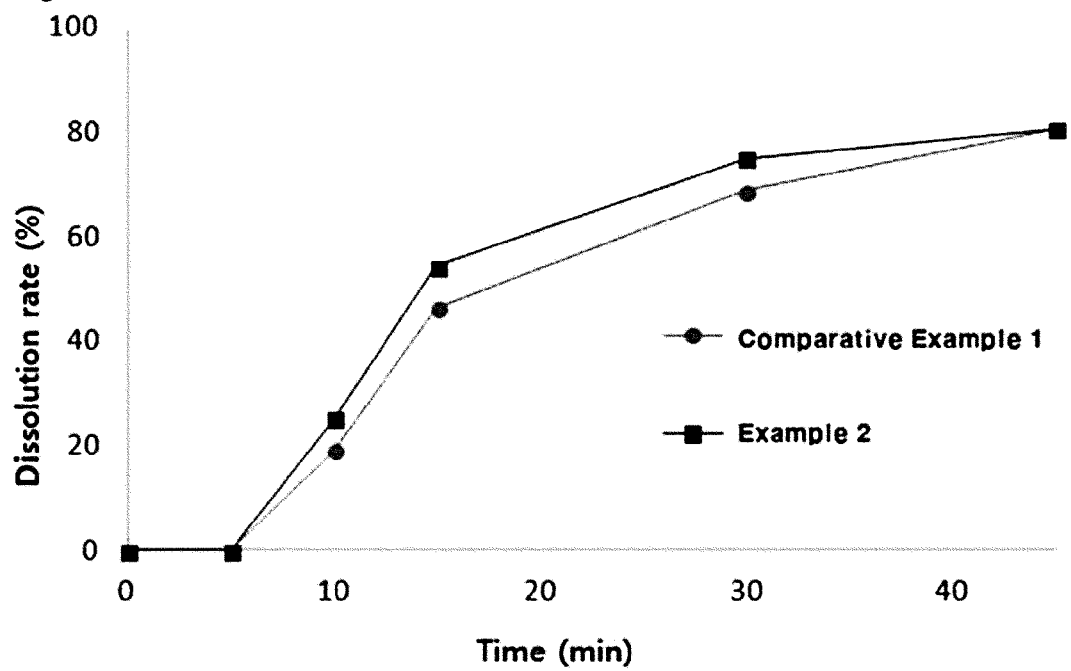

PHARMACEUTICAL COMPOSITION COMPRISING DUTASTERIDE AND PROPYLENE GLYCOL MONOLAURATE AND PREPARATION METHOD OF THE SAME

TECHNICAL FIELD

The present disclosure relates to a pharmaceutical composition comprising dutasteride, a capsule formulation comprising the same, and a preparation method of the same. More particularly, the present invention further relates to a pharmaceutical formulation reducing the size of the capsule with improved stability.

BACKGROUND ART

U.S. Pat. No. 5,565,467 discloses that dutasteride (chemical name: 17β-N-(2,5-bis(trifluoromethyl))phenylcarbamoyl-4-aza-5α-androst-1-en-3-one) of the following Formula (I), a 5-alpha reductase inhibitor, is capable of being used in treating benign prostate hyperplasia, prostate cancer and male pattern alopecia (androgenetic alopecia).

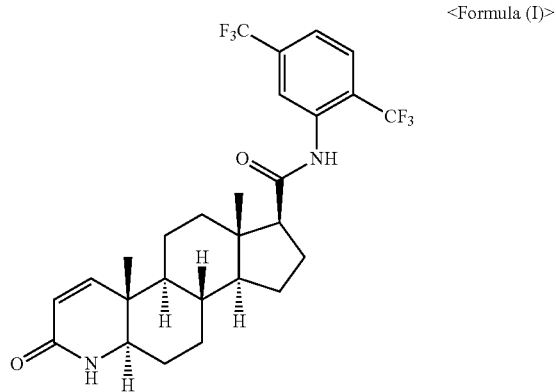

<Formula (I)>

Dutasteride is commercially available as AVODART® soft gelatin capsule (size of 6 oblong) which contains 0.5 mg of dutasteride dissolved in 349.5 mg of a mixture of mono- and di-glyceride of caprylic/capric acid and butylated hydroxy toluene (BHT).

However, in order to fill the active ingredient, dutasteride into the soft gelatin capsule, a large amount of oils and surfactants are required to be used, leading to an increase in the size of the capsule. The large-sized capsule may cause low patient compliance due to patient's inability or unwillingness to swallow the large-sized formulations. In particular, considering that the great majority of benign prostate hyperplasia patients is elderly patients and long-term use of dutasteride is required for the treatment, the large size of the dutasteride capsule leads to disadvantages in that taking such large capsule is very inconvenient for elderly patients and thus patient compliance is low.

Korean Patent No. 10-1055412 discloses a method for preparing a tablet of dutasteride by using a self-emulsifying drug delivery system. However, in order to prepare tablets with improved dissolution characteristics of poorly water-soluble drug, dutasteride, additional excipients such as surfactants and absorbents are needed and the preparation method is somehow complicated as the two-times coating is required. Further, a large amount of absorbents are required, leading to an increase in the size of the capsule which is likely to cause the problem in patient compliance.

Korean Patent Publication No. 10-2013-0086551 discloses a method of improving solubility and bioavailability of dutasteride by using a self-emulsifying drug delivery system. However, a large amount of surfactant (equal to or more than 20% of total composition) is used in the self-emulsifying drug delivery system, thereby causing low stability (decrease in moisture and increase in hardness of gelatin used as a capsule base and the subsequent delayed disintegration and low dissolution rate).

The present inventors of the present invention have conducted a research on formulation of dutasteride to develop a pharmaceutical composition having smaller content in the capsule than that of AVODART® capsule, and having excellent stability even though the amount of the capsule content to be filled is low. They discovered that propylene glycol monolaurate is used as an excellent solubilizer that dissolves dutasteride, thereby causing decrease in the size of the dutasteride capsule, while ensuring an equivalent dissolution rate as that of AVODART®, as well as an improved stability.

DISCLOSURE OF INVENTION

Technical Problem

The present disclosure provides a pharmaceutical composition comprising dutasteride which is characterized by improved solubility of dutasteride, the reduction in the capsule size, and improved stability, and a preparation method of the same.

The technical problem of the present disclosure are not limited to the technical problem described above, and other technical problems that are not described will be clear to those skilled in the art from the description provided below.

Solution to Problem

In one aspect, the present disclosure relates to a pharmaceutical composition comprising dutasteride and propylene glycol monolaurate.

According to one embodiment of the present pharmaceutical composition, the content of dutasteride is greater than or equal to 0.1% by weight and less than or equal to 3.0% by weight, and the content of propylene glycol monolaurate is greater than or equal to 97.0% by weight and less than or equal to 99.9% by weight based on the total of the pharmaceutical composition.

According to another embodiment of the present pharmaceutical composition, the pharmaceutical composition further comprises pharmaceutically acceptable excipients.

In another aspect, the present disclosure relates to a capsule formulation comprising the pharmaceutical composition. The capsule formulation is soft or hard capsule fomulation.

According to one embodiment of the present capsule formulation, the pharmaceutical composition is filled in a liquid phase.

In another aspect, the present disclosure relates to a method of preparing the capsule formulation, comprising dissolving dutasteride in propylene glycol monolaurate to obtain a clear solution of dutasteride; and filling the obtained clear solution in a capsule.

Other embodiments of the present disclosure are included in the detailed description and the drawings.

Advantageous Effects of Invention

The present pharmaceutical composition comprising dutasteride uses propylene glycol monolaurate, which has high solubility and stability to dutasteride, as a solubilizer, thereby solving the problem of the poor solubility of dutasteride, reducing the size of the dutasteride capsule formulation, improving patient compliance, and increasing stability of dutasteride.

Effects of the present disclosure are not limited to the effects illustrated above, and more various effects are included in the present specification.

BRIEF DESCRIPTION OF DRAWINGS

FIG. 1 shows the comparison of the appearance of a capsule prepared according to one embodiment of the present disclosure and a commercially-available AVODART® capsule.

FIG. 2 shows a graph of dissolution rate comparison tests of comparative examples and an example of the present disclosure.

MODE FOR THE INVENTION

The present disclosure provides a pharmaceutical composition comprising dutasteride and propylene glycol monolaurate. That is, the present invention relates to a pharmaceutical composition in which the solubility of the poorly-soluble drug, dutasteride is improved, thereby reducing the size of the final oral capsule formulation, and hence improving the patient's compliance, while ensuring capsule stability to have an equivalent dissolution rate as that of an existing product; a method of manufacturing the pharmaceutical composition; and an oral capsule formulation filled with the pharmaceutical composition. The capsule formulation according to one embodiment of the present disclosure is expected to exhibit characteristics of rapid absorption and excellent stability upon oral administration.

In the pharmaceutical composition comprising dutasteride according to one embodiment of the present disclosure, propylene glycol monolaurate is used as a capsule filling oil component because propylene glycol monolaurate exhibits excellent solubility improvement effects of an active ingredient, dutasteride, and has characteristics as a pharmaceutically acceptable excipient capable of ensuring the stability of dutasteride when dissolved. One embodiment of the present disclosure may further use an antioxidant that may enhance stabilization of propylene glycol monolaurate, and the like.

Hereinafter, detailed composition of the pharmaceutical composition according to one embodiment of the present disclosure and a method of manufacturing the pharmaceutical composition will be described with reference to embodiments and comparative examples.

Test Example 1 is a test result comparing the solubility of dutasteride depending on the types of oil. As identified in Table 5 of Test Example 1, dutasteride, an active ingredient of the present disclosure, is not favorably soluble in oil such as glycerol tricaprylate, glycerol tricaprylate/caprate, glycerol tricaprylate/caprate/linoleate, propylene glycol dicaprylocaprate, propylene glycol dicaprate, and propylene glycol dicaprylate. However, the solubility of dutasteride is much higher in propylene glycol monolaurate than that in other oils.

In Test Example 2, in order to identify the stability of dutasteride in oil, the oil and dutasteride are mixed at a ratio of about 10 to 1, and then a stability test is carried out under an accelerated and stress condition, and a percentage of generated unknown degradation products with respect to the active ingredient is calculated to confirm whether degradation products are generated or not.

As shown in the following Table 6, the stability of dutasteride in oil is identified as follows: a relatively large amount of degradation products is generated in mono- and di-glyceride of caprylic/capric acid used in an existing AVODART® soft capsule under both accelerated and stress conditions. However, degradation products were not generated in propylene glycol monolaurate even when stored under the accelerated condition for 4 weeks. In addition, even when stored under the stress condition for 4 weeks, a relatively small amount of degradation products is generated, as compared to that in mono- and di-glyceride of caprylic/capric acid.

Based on the solubility and stability tests, it was identified that propylene glycol monolaurate is capable of enhancing solubility and stability of dutasteride in the pharmaceutical composition according to one embodiment of the present disclosure.

In addition, the composition according to one embodiment of the present disclosure may use a pharmaceutically acceptable excipient for oral administration, for example, an antioxidant, an colorant, and a preservative, within the scope that does not obscure the purpose of the present disclosure. Example of the antioxidant may include butylated hydroxy toluene (BHT), butylated hydroxy anisole (BHA) and the like.

In addition, embodiments of the present disclosure also provide a method of manufacturing a pharmaceutical composition comprising dutasteride that comprises a step of dissolving dutasteride in propylene glycol monolaurate. In the aforementioned manufacturing method, dutasteride and propylene glycol monolaurate may be mixed so that dutasteride is homogeneously dissolved in propylene glycol monolaurate in a liquid phase.

In addition, embodiments of the present disclosure provide an oral capsule formulation filled with the pharmaceutical composition comprising dutasteride. The pharmaceutical composition may be manufactured as a soft capsule formulation using a capsule base such as a generally used gelatin (or succinylated gelatin) and a plasticizer (e.g., glycerin, citric acid, sorbitol solution, glycine and propylene glycol) and using a conventional rotary type automatic filler.

In addition, the pharmaceutical composition may be filled into a hard capsule, using a hard capsule manufacturing apparatus for liquid filling. Examples of bases used in the hard capsule may include gelatin/hydroxypropylmethylcellulose and a plasticizer (e.g., glycerin, citric acid, sorbitol solution, glycine and propylene glycol).

The amount of the pharmaceutical composition being filled in the oral capsule formulation can be 92 mg to 185 mg, preferably 100 mg to 150 mg, more preferably 110 mg. The oral capsule formulation of the present disclosure can be prepared in size 2 oval (minims: 1.5-1.8, cc: 0.092-0.111), size 3 oval (minims: 2.4-3.0, cc: 0.148-0.185), size 3 oblong (minims: 2.3-3.0, cc: 0.142-0.185), size 4 oblong (minims: 3.0-4.0, cc: 0.185-0.246) and the like.

The oral capsule formulation filled with the pharmaceutical composition comprising dutasteride according to one embodiment of the present disclosure has a relatively small size and an equivalent dissolution rate as compared to those of AVODART®, a commercial formulation, through the use of propylene glycol monolaurate which may enhance solubility and stability of dutasteride. When referring to FIG. 1, the size of the oral capsule formulation according to one embodiment of the present disclosure is 2 oval (see the left picture in FIG. 1), and is smaller compared to size 6 oblong of AVODART® (minims: 5.0-6.0, cc: 0.308-0.370, see the right picture in FIG. 1). Further, when referring to FIG. 2, the dissolution rate of the oral capsule formulation according to one embodiment of the present disclosure (see the square shape in FIG. 2) is equivalent as compared to those of AVODART® (see the round shape in FIG. 2).

Hereinafter, embodiments of the present disclosure will be described in more detail. The present disclosure may, however, be embodied in many different forms and should not be construed as being limited to the embodiments set forth herein.

EXAMPLE 1

To a 3 L preparation container equipped with a stirrer, 1,094.9 g of propylene glycol monolaurate was added, and while stirring, 5 g of dutasteride was slowly added thereto and completely dissolved. 0.1 g of butylated hydroxy toluene was added thereto, and the resultant mixture was stirred to manufacture a pharmaceutical composition comprising dutasteride. Separately, to prepare a soft capsule shell, a shell-forming agent was prepared using gelatin, a plasticizer and the like according to the composition shown in the following Table 1. After filling a size 2 oval soft capsule with 110 mg of the prepared solubilized composition using a rotary type automatic filler to a total weight of 230 mg, drying and sorting processes were carried out to manufacture an oral soft capsule formulation.

TABLE 1

| Composition of oral soft capsule shell | |
|---|---|
| Content | Weight (g) |
| Gelatin | 833.2 |
| Concentrated glycerin | 256.7 |
| D-sorbitol solution | 110.1 |
| Total | 1200.0 |

EXAMPLE 2

To a 3 L preparation container equipped with a stirrer, 194.9 g of propylene glycol monolaurate was added, and while stirring, 5 g of dutasteride was slowly added thereto and completely dissolved. 0.1 g of butylated hydroxy toluene was added thereto, and the resultant mixture was stirred to manufacture a pharmaceutical composition comprising dutasteride. Separately, to prepare a soft capsule shell, a shell-forming agent was prepared using succinylated gelatin, a plasticizer and the like according to the composition shown in the following Table 2. After filling a size 2 oval soft capsule with 110 mg of the prepared solubilized composition using a rotary type automatic filler to a total weight of 230 mg, drying and sorting processes were carried out to manufacture an oral soft capsule formulation.

TABLE 2

| Composition of oral soft capsule shell | |
|---|---|
| Content | Weight (g) |
| Succinylated gelatin | 854.0 |
| Concentrated glycerin | 242.0 |
| D-sorbitol solution | 104.0 |
| Total | 1200.0 |

EXAMPLES 3 TO 9

To a 500 mL preparation container equipped with a stirrer, oils were added in the amounts shown in the following Table 3, and while stirring, 0.5 g of dutasteride was slowly added thereto and completely dissolved. Separately, to prepare a soft capsule shell, a shell-forming agent was prepared using succinylated gelatin, a plasticizer and the like according to the composition shown in the above Table 2. After filling the composition manufactured according to Table 3 using a rotary type automatic filler, drying and sorting processes were carried out to manufacture an oral soft capsule formulation.

TABLE 3

| Content (g/formulation) | Example 3 | Example 4 | Example 5 | Example 6 | Example 7 | Example 8 | Example 9 |
|---|---|---|---|---|---|---|---|
| Dutasteride | 0.5 g | 0.5 g | 0.5 g | 0.5 g | 0.5 g | 0.5 g | 0.5 g |
| Propylene glycol monolaurate | 104 g | 150 g | 220 g | 150 g | 220 g | 160 g | 220 g |
| Soft capsule size | 2 round | 3 round | 4 round | 3 oval | 4 oval | 3 oblong | 4 oblong |

EXAMPLES 10 AND 11

To a 500 mL preparation container equipped with a stirrer, oils were added in the amounts shown in the following Table 4, and while stirring, 0.5 g of dutasteride was slowly added thereto and completely dissolved. Separately, to prepare a soft capsule shell, a shell-forming agent was prepared using succinylated gelatin, a plasticizer and the like according to the composition shown in the above Table 2. After filling the composition manufactured according to Table 4 using a rotary type automatic filler, drying and sorting processes were carried out to manufacture an oral soft capsule formulation.

TABLE 4

| Content (g/formulation) | Example 10 | Example 11 |
|---|---|---|
| Dutasteride | 0.5 g | 0.5 g |
| Propylene glycol monolaurate | 49.5 g | 29.5 g |
| Soft capsule size | 2 round | 2 round |

COMPARATIVE EXAMPLE 1

Commercially Available Formulation

A currently commercially-available AVODART® 0.5 mg soft capsule corresponding to 0.5 mg of dutasteride was used.

TEST EXAMPLE 1

Evaluation of Oil Solubility

In order to measure the solubility of dutasteride in oil, the solubility of dutasteride in glycerol tricaprylate, glycerol tricaprylate/caprate, glycerol tricaprylate/caprate/linoleate, propylene glycol dicaprylocaprate, propylene glycol dicaprate, propylene glycol dicaprylate and propylene glycol monolaurate was measured. In a 10 mL vial, a magnetic bar was placed. After 3 mL of the oil was added thereto, approximately 100 mg of dutasteride was added thereto while stirring under a room temperature (25° C.) condition, and the resultant mixture was stirred at 500 rpm or higher. After stirring for 24 hours, 1 mL of the resultant mixture was taken and separated using a centrifuge, and only a supernatant was taken to quantify an amount of dutasteride dissolved in the oil using liquid chromatography. As for the solubility in each oil obtained from the test results, propylene glycol monolaurate exhibited higher solubility by 10 times or greater compared to other tested oils, as shown in Table 5.

TABLE 5

Solubility of dutasteride depending on oil type

| Oil | Solubility (mg/mL) |
|---|---|
| Glycerol tricaprylate | 0.84 |
| Glycerol tricaprylate/caprate | 0.81 |
| Glycerol tricaprylate/caprate/linoleate | 0.22 |
| Propylene glycol dicaprylroccaprate | 0.97 |
| Propylene glycol dicaprate | 0.77 |
| Propylene glycol dicaprylate | 1.13 |
| Propylene glycol monolaurate | 10.43 |

TEST EXAMPLE 2

Test on Stability of Dutasteride Depending on Oil Type

In order to identify the stability of dutasteride in mono- and di-glyceride of caprylic/capric acid used as an oil phase of AVODART®, an existing commercially-available formulation, the stability of dutasteride was compared under the stress condition (50° C., 95% RH) and the accelerated condition (40° C., 75% RH). In the comparison test, a sample prepared by dissolving 1.0 mg of dutasteride in 10.0 mg of propylene glycol monocaprylate and stored in a transparent vial and a sample prepared by dissolving 1.0 mg of dutasteride in 10.0 mg of mono- and di-glyceride of caprylic/capric acid and stored in a transparent vial were used. A percentage of degradation products with respect to dutasteride, an active ingredient, was calculated and summarized in the following Table 6.

TABLE 6

Stability results of dutasteride depending on oil type

| | Stress condition(50° C., 95% RH) | | | | Accelerated condition(40° C., 75% RH) |
|---|---|---|---|---|---|
| | Week 1 | Week 2 | Week 3 | Week 4 | Week 4 |
| Propylene glycol monolaurate | None | None | None | 0.32% | None |
| mono- and di-glyceride of caprylic/capric acid | None | None | None | 1.75% | 0.94% |

As can be identified from Table 6, the stability of dutasteride in propylene glycol monolaurate was more superior compared to that in mono- and di-glyceride of caprylic/capric acid in the week 4 under the accelerated condition (40, 75% RH) and the stress condition (50° C., 95% RH).

TEST EXAMPLE 3

Comparative Dissolution Test with AVODART®

A dissolution evaluation was carried out on the oral soft capsule formulation filled with the composition of self-emulsifying drug delivery system manufactured in the above Example 2 and the commercially-available AVODART® 0.5 mg soft capsule of Comparative Example 1. The dissolution test was carried out in accordance with Method 2 of the dissolution test method in the Korean Pharmacopoeia 10th edition using a 0.3% aqueous lauryl sodium sulfate solution as an eluent and a rotation speed of 50 rpm.

TABLE 7

Result of dissolution evaluation

| | Example 2 (%) | Comparative Example 1 (%) |
|---|---|---|
| 5 minutes | 0 | 0 |
| 10 minutes | 25.2 | 19.3 |
| 15 minutes | 54.3 | 46.3 |
| 30 minutes | 74.9 | 68.8 |
| 45 minutes | 80.6 | 80.6 |

As shown in the above Table 7 and FIG. 2, it was identified that the oral soft capsule formulation of Example 2 of the present disclosure had a dissolution rate similar to that of AVODART® of Comparative Example 1. Accordingly, according to one embodiment of the present disclosure, a soft capsule formulation for oral administration filled with the pharmaceutical composition comprising dutasteride that is reduced in size but has an equivalent dissolution rate as compared to those of the existing formulation has been developed.

The invention claimed is:
1. A pharmaceutical composition comprising dutasteride of the following Formula (I) and propylene glycol monolaurate:

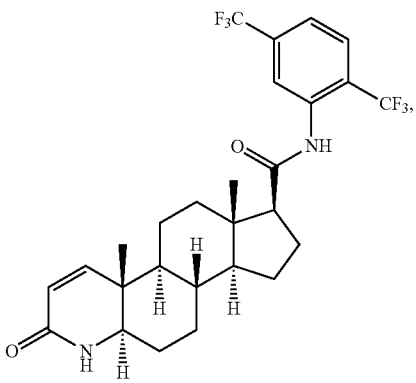

<Formula (I)> wherein the content of dutasteride is greater than or equal to 0.1% by weight and less than or equal to 3.0% by weight, and the content of propylene glycol monolaurate is greater than or equal to 97.0% by weight and less than or equal to 99.9% by weight based on the total of the pharmaceutical composition, and wherein the pharmaceutical composition does not comprise a surfactant.

2. The pharmaceutical composition of claim 1, further comprising a pharmaceutically acceptable excipient.

3. An oral soft or hard capsule formulation comprising the pharmaceutical composition of claim 2.

4. The capsule formulation of claim 3, wherein the pharmaceutical composition is filled in a liquid phase.

5. An oral soft or hard capsule formulation comprising the pharmaceutical composition of claim 1.

6. The capsule formulation of claim 5, wherein the pharmaceutical composition is filled in a liquid phase.

7. A method of preparing an oral capsule formulation of dutasteride, comprising:
  filling a capsule with the pharmaceutical composition of claim 1.

* * * * *